(12) United States Patent
Mann et al.

(10) Patent No.: US 9,289,576 B2
(45) Date of Patent: Mar. 22, 2016

(54) CATHETER ASSEMBLY

(75) Inventors: James W. Mann, Elkton, MD (US);
Sherif A. Eskaros, Elkton, MD (US);
Eric C. Lafferty, Bear, DE (US); David J. Messick, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 281 days.

(21) Appl. No.: 10/871,718

(22) Filed: Jun. 17, 2004

(65) Prior Publication Data
US 2005/0283221 A1     Dec. 22, 2005

(51) Int. Cl.
*A61F 2/958*    (2013.01)
*A61M 25/00*    (2006.01)
*A61M 25/10*    (2013.01)
*A61M 25/01*    (2006.01)

(52) U.S. Cl.
CPC ....... *A61M 25/0054* (2013.01); *A61M 25/0023* (2013.01); *A61M 25/0029* (2013.01); *A61M 25/0045* (2013.01); *A61M 25/10* (2013.01); *A61M 2025/0037* (2013.01); *A61M 2025/0039* (2013.01); *A61M 2025/0183* (2013.01)

(58) Field of Classification Search
CPC ..................... A61M 25/0054; A61M 25/0029; A61M 25/0023; A61M 25/10; A61M 25/0045; A61M 202/0039; A61M 2025/0037; A61M 2025/0183
USPC ........ 604/93.01, 94.01, 95.02, 96.01, 103.04, 604/164.13, 263, 523, 524, 526, 527, 604/103.09; 606/192, 194, 190, 191; 623/1.11, 6.11
See application file for complete search history.

(56) References Cited

U.S. PATENT DOCUMENTS

| | | | |
|---|---|---|---|
| 3,953,566 A | 4/1976 | Gore | 264/288 |
| 4,187,390 A | 2/1980 | Gore | 174/102 R |
| 4,516,972 A | 5/1985 | Samson | 604/282 |
| 4,988,356 A * | 1/1991 | Crittenden et al. | 606/192 |
| 5,334,147 A | 8/1994 | Johnson | 604/96 |
| 5,370,615 A * | 12/1994 | Johnson | 604/102.02 |

(Continued)

FOREIGN PATENT DOCUMENTS

| | | |
|---|---|---|
| EP | 1103281 | 11/2000 |
| EP | 1374943 | 6/2003 |

(Continued)

OTHER PUBLICATIONS

U. S. Appl. No. 10/402,083, filed Mar. 28, 2003, entitled "A Puncturable Catheter," Armstrong et al.

*Primary Examiner* — Ashley Fishback
(74) *Attorney, Agent, or Firm* — Allan M. Wheatcraft

(57) ABSTRACT

Catheter having a proximal section and a distal section. The proximal section having at least a delivery lumen and a guidewire receiving lumen, the guidewire receiving lumen having a proximal guidewire exit port at a location proximal of the distal end of the proximal section. A reinforcing tubular member located in the proximal section delivery lumen extending from substantially the proximal end of the proximal section to a point distal to the proximal guidewire exit port, wherein the reinforcing tubular member transitions from relatively rigid to relatively more flexible from a proximal point to a distal point thereon and has an outer diameter equal to about the inner diameter of the delivery lumen for at least a portion of the reinforcing tubular member that extends distal to the proximal guidewire exit port. The distal section having at least a delivery lumen and a guidewire receiving lumen.

16 Claims, 5 Drawing Sheets

(56) References Cited

U.S. PATENT DOCUMENTS

| | | | |
|---|---|---|---|
| 5,380,283 A | 1/1995 | Johnson | 604/96 |
| 5,472,425 A | 12/1995 | Teirstein | 604/102 |
| 5,476,589 A | 12/1995 | Bacino | 210/500.36 |
| 5,489,271 A * | 2/1996 | Andersen | 604/103.04 |
| 6,027,487 A | 2/2000 | Crocker | 604/508 |
| 6,159,195 A * | 12/2000 | Ha et al. | 604/500 |
| 6,159,565 A | 12/2000 | Campbell et al. | 428/35.7 |
| 6,248,092 B1 | 6/2001 | Miraki et al. | 604/96.01 |
| 6,319,228 B1 * | 11/2001 | Kastenhofer | 604/96.01 |
| 6,398,799 B2 * | 6/2002 | Kramer | 606/194 |
| 6,589,207 B1 | 7/2003 | El-Nounou | |
| 6,733,486 B1 | 5/2004 | Lee et al. | 604/525 |
| 6,887,219 B2 * | 5/2005 | Wantink | 604/103.04 |
| 7,037,291 B2 * | 5/2006 | Lee et al. | 604/103.04 |
| 7,273,470 B2 * | 9/2007 | Wantink | 604/103.04 |
| 2002/0007146 A1 * | 1/2002 | Omaleki et al. | 604/103.09 |
| 2003/0191491 A1 * | 10/2003 | Duane et al. | 606/194 |
| 2004/0054323 A1 | 3/2004 | Wantink | 604/103.04 |

FOREIGN PATENT DOCUMENTS

| | | |
|---|---|---|
| JP | 2001-353225 | 12/2001 |
| JP | 2002/204831 | 7/2002 |
| JP | 2002-355313 | 12/2002 |
| JP | 2004-24625 | 1/2004 |
| WO | 02/096483 | 12/2002 |
| WO | 03/084592 | 10/2003 |

* cited by examiner

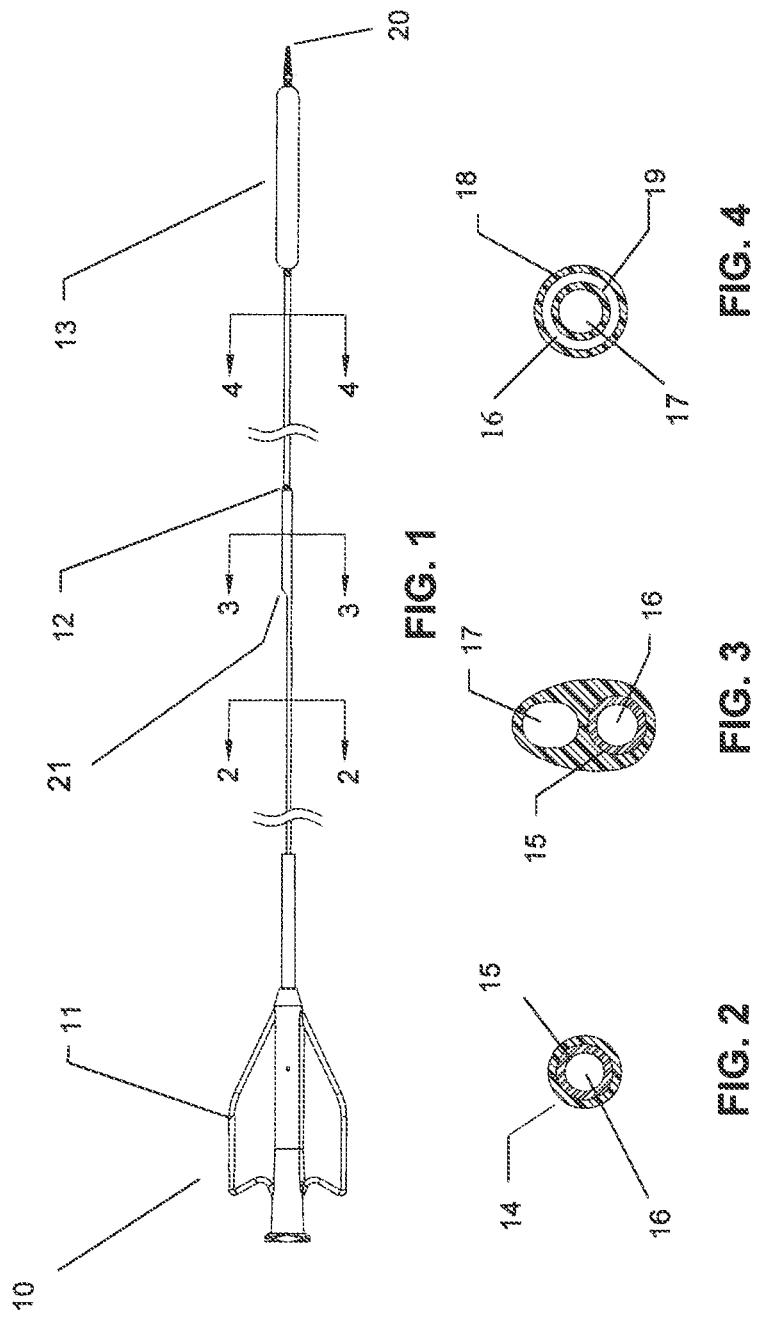

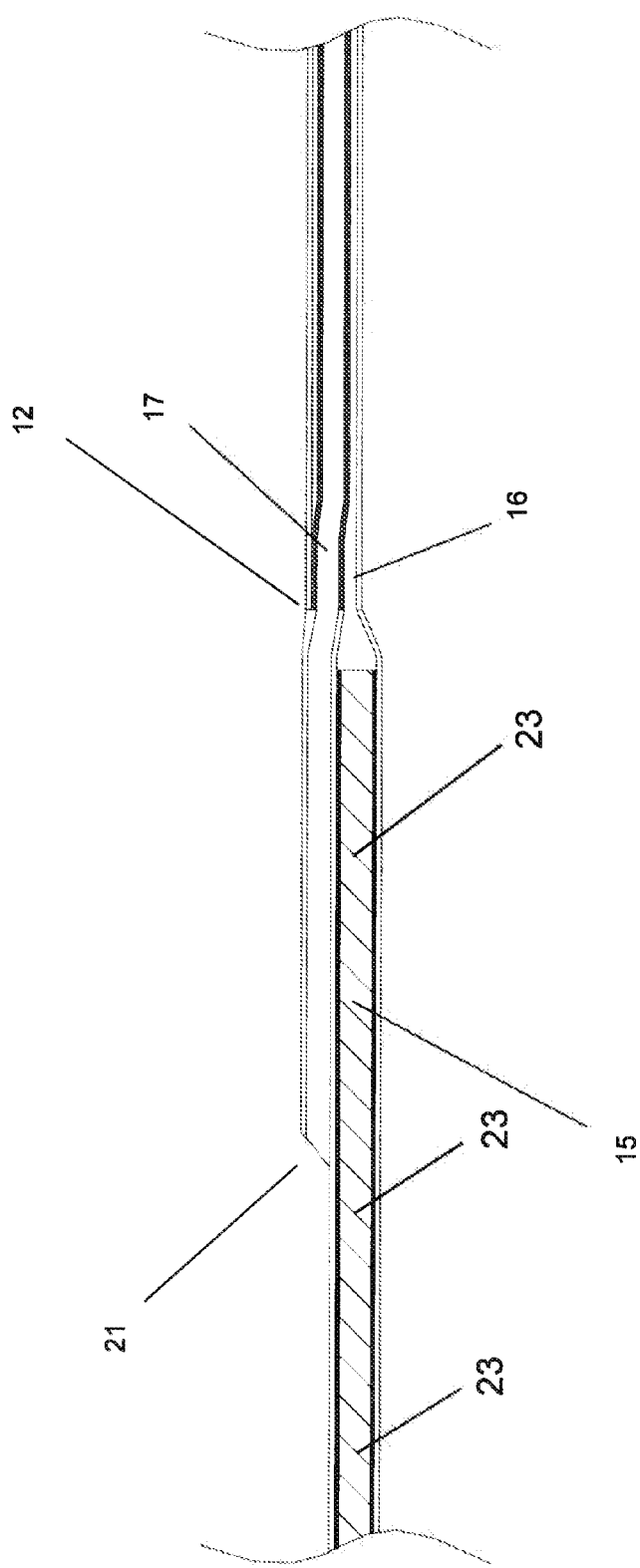

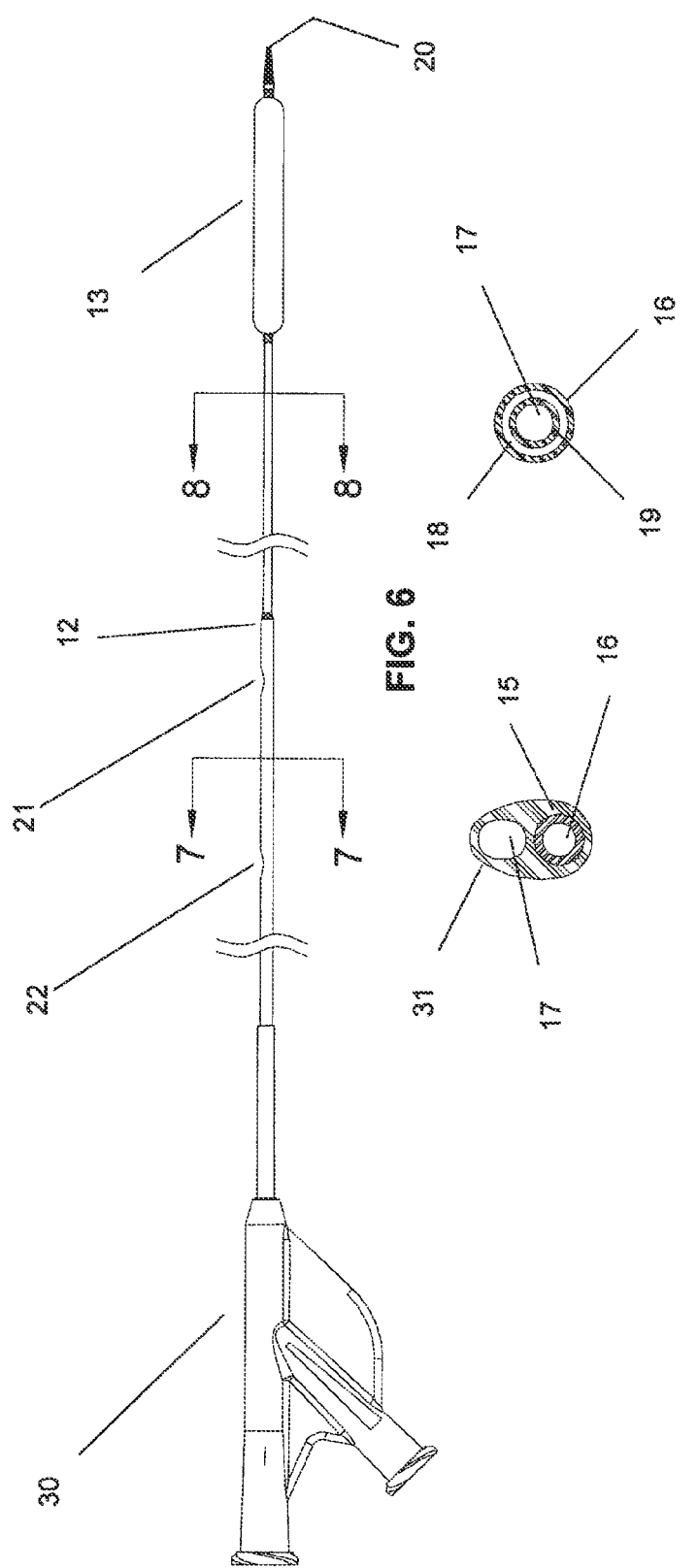

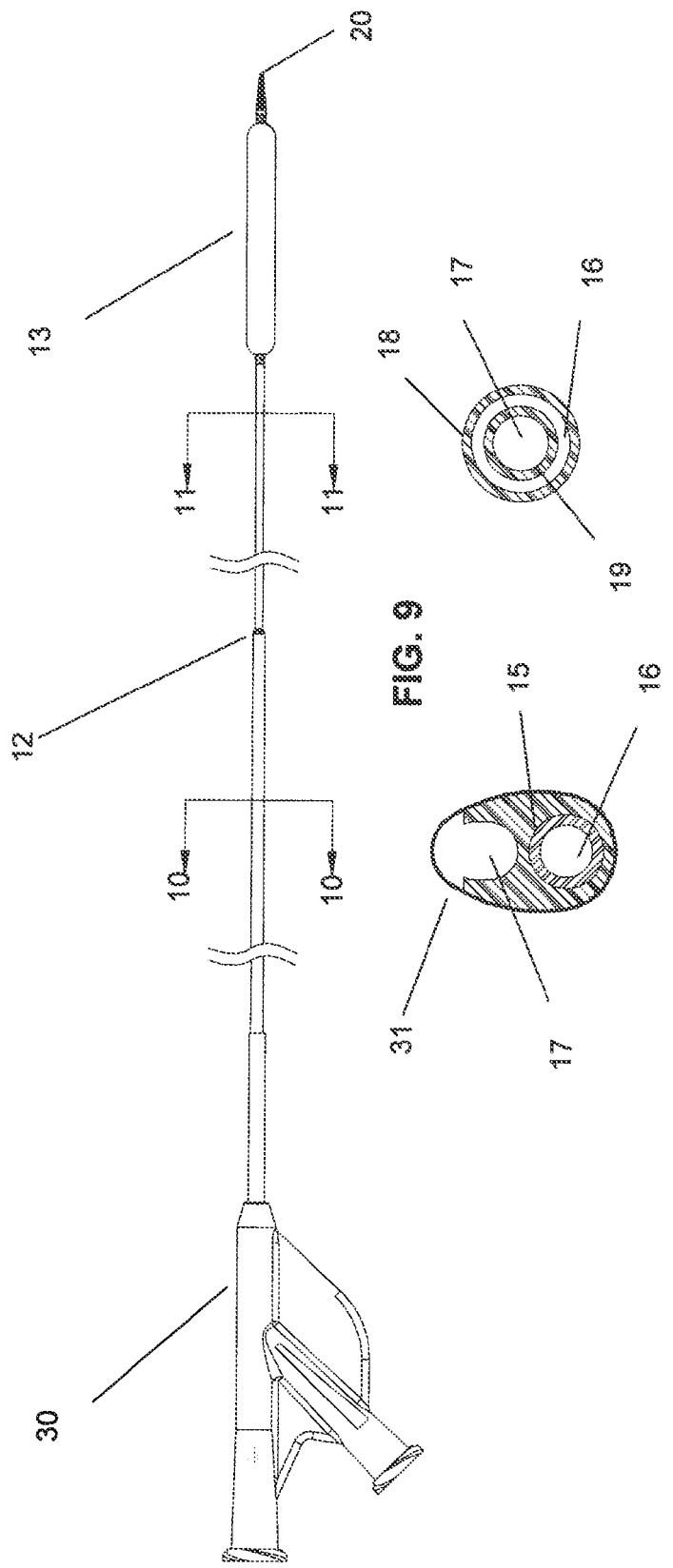

CATHETER ASSEMBLY

FIELD OF THE INVENTION

The present invention relates to catheters having at least a guide wire lumen and a delivery lumen.

BACKGROUND OF THE INVENTION

A variety of different therapies can be delivered within the human body by catheter devices. Therapeutic devices such as dilatation balloons, stents, and embolic filters, and therapeutic agents such as drugs and radiation sources, may be positioned at or near the distal end of the catheter for delivery to a desired site within the body.

The prior art discloses numerous examples of intravascular catheters. Such catheters have found particular utility for procedures such as angioplasty and stent deployment. Of particular interest recently is improving catheters for use in percutaneous transluminal coronary angioplasty (PTCA) procedures. In typical PTCA procedures a guiding catheter is advanced in the patient's vasculature until the distal tip of the guiding catheter is seated in the ostium of a desired coronary artery. A guide wire is first advanced out of the distal end of the guiding catheter into the patient's coronary artery until the distal end of the guide wire crosses a lesion to be dilated. A dilatation catheter, having an inflatable balloon on the distal portion thereof, is advanced into the patient's coronary artery over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery (i.e. reformation of the arterial blockage) which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted state on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion.

With regard to coronary catheters, two main types of catheter designs, over-the-wire (OTW) and rapid-exchange (RX), dominate these applications. Each of these designs has its advantages and disadvantages. OTW catheters track over their entire length on a guidewire, which allows them to follow the wire easily and allows the direct transmission of longitudinal force over the guidewire. Additionally, these catheters allow for guidewires to be exchanged once the catheter has been advanced into position, which may be desirable when different guidewire attributes (e.g., tip curvature or radiopaque markers) are needed. However, these systems require the use of a long guidewire (e.g., 300 cm in length) and cannot be effectively operated by one person.

RX catheters typically use shorter guidewires (e.g., 180 cm in length) which allow the catheter to be operated by a single physician. The physician is able to hold the guide catheter and guidewire with one hand while using his/her other hand to advance or retract the catheter along the guidewire. However, because the entire length of the RX catheter does not slide over the guidewire, the direct transmission of longitudinal force along the path of the guidewire may be compromised, and wire exchange can not be performed once the proximal catheter guidewire port is advanced into the patient. Another problem with the design of RX catheters is that, compared to traditional OTW catheters, it results in catheters which have inferior pushability and also tend to buckle and/or kink—especially at or near the proximal (or rapid-exchange) guide wire exit port.

More recently introduced coronary catheters are hybrids of the OTW and RX catheters, sometimes referred to as "convertible" catheters. For example, U.S. Pat. Nos. 5,334,147 and 5,380,283 to Johnson teach the construction of a balloon catheter having a proximal portion that includes an aperture through the wall of the catheter into the guidewire lumen. The aperture is covered by a frangible wall (e.g., a thin-walled tube sealed to the catheter body in a position to cover the aperture portion). The frangible wall may be punctured by a guidewire, allowing the guidewire to exit the catheter guidewire lumen via the aperture. Thus, providing both rapid-exchange and over-the-wire capabilities.

U.S. Pat. No. 5,472,425 to Teirstein describes a catheter having a guidewire lumen covered by a rupturable membrane that extends along substantially the entire length of the catheter, whereby the membrane may be intentionally punctured at any desired location by the guidewire. Thus, providing both rapid-exchange and over-the-wire capabilities. The use and general construction of the catheter are related, although no materials or specific constructions for the rupturable membrane are taught.

Commonly owned and co-pending U.S. patent application Ser. No. 10/402,083, filed on Mar. 28, 2003, to Armstrong et al describes a unique convertible catheter that comprises a guidewire lumen having a thin covering that is easily punctured to form a guidewire exit port at virtually any desired point along the catheter. The thin covering may be integral with the catheter shaft, or may be a separate component that covers only the portion of the catheter shaft immediately adjacent the outer portion of the guidewire lumen, or may be a thin tubular construct that surrounds the entire catheter shaft. In one disclosed embodiment the thin covering is made from a thin tape of porous expanded polytetrafluoroethylene (ePTFE) helically wrapped about the exterior of a catheter shaft. The wrapping can be accomplished, for example, in two opposing directions parallel to the length of the catheter shaft, resulting in a bias-ply construction. This thin covering offers good transparency and is easily punctured (e.g., by the end of a guidewire) and yet is resistant to tearing at the puncture site. Other disclosed materials for the thin covering include, for example, polyethylene terephthalate (PET), polyethylene, polypropylene, polyamide, etc. Porous polymers, optionally provided with a thin, non-porous coating, may be advantageously used because of their excellent flexibility. Most preferred are tapes made from thin ePTFE film that has been provided with a porous or non-porous coating of a thermoplastic such as a thermoplastic fluoropolymer, preferably fluorinated ethylene propylene (FEP). Exemplary ePTFE films can be made as taught by U.S. Pat. Nos. 3,953,566 and 4,187,390 to Gore. More preferred are ePTFE films made as taught be U.S. Pat. No. 5,476,589 to Bacino. The construction of thin, helically-wrapped tubes from ePTFE films and thermoplastic-coated ePTFE films, and the method of providing the coating onto the ePTFE films, are taught, for example, by U.S. Pat. No. 6,159,565 to Campbell et al. The guidewire lumen can be in the form of a slot made into the catheter shaft, with the slot provided with the thin covering. Preferably, the slot extends for most or even all of the length of the catheter. The slot can be covered with a thin tubular covering that coaxially encloses the entire catheter shaft or alternatively a strip of thin tape-like covering material that covers the slot and is adhered to the surface of the catheter shaft immediately adjacent both sides of the slot. A multiplicity of pre-formed openings may be provided through the thin covering if desired. Also, the slot covering material may take the form of a braid or winding of filaments. This braid or winding of filaments may optionally be covered with a thin polymeric tube except for the filaments immediately over the top of the slot which preferably remain exposed and allow for passage of the end of a guidewire through any interstice between adjacent filaments.

A further problem with conventional balloon catheters for intravascular procedures, such as angioplasty and stent delivery, is such catheters frequently have stiff proximal sections to facilitate advancement of the catheter within the patient's body lumen and relatively flexible distal shaft sections to facilitate passage through tortuous anatomy such as distal coronary and neurological arteries without damage to the luminal wall. Typically, there is an intermediate shaft section or junction between the relatively stiff proximal shaft section and the relatively flexible distal shaft section that provides a transition between the proximal shaft section and the distal shaft section.

A variety of proposed solutions to the problems of providing catheters with rapid-exchange capabilities, good pushability, smooth flexibility transition from proximal end to distal end, and good resistance to buckling and/or kinking (especially at the proximal (or rapid-exchange) guide wire exit port) have been attempted. However, the search continues for a catheter that overcomes all of these problems.

SUMMARY OF THE INVENTION

Catheters having at least two lumens are disclosed. The catheter includes a proximal section and a distal section. The proximal section and distal section may be joined together at a joint, or the sections may be a single piece formed by, for example, extruding plastic material. The proximal section includes at least a delivery lumen extending from the proximal end (or near the proximal end) to the distal end thereof. Located in at least a portion of the proximal section delivery lumen is reinforcing tubular member, which is positioned to structurally support the wall of the proximal section delivery lumen of the catheter. The reinforcing tubular member is constructed or configured to transition from being relatively rigid at a proximal point to being relatively more flexible at a distal point. In an aspect of the invention the reinforcing tubular member transitions from being relatively rigid at substantially its proximal end to being relatively flexible at its distal end. In an aspect of the invention, the reinforcing tubular member may extend from the proximal end of the proximal section to (or close to) the distal end.

The proximal section of the catheter also includes a guidewire receiving lumen. The guidewire receiving lumen may extend from the distal end of the proximal section to a point distal of the proximal end, or the guidewire receiving lumen may extend from the distal end of the proximal section to the proximal end thereof. The guidewire receiving lumen includes at least one proximal guidewire exit port located proximally from the distal end of the proximal section. The reinforcing tubular member extends to a point distal of the proximal guidewire exit port, and has an outer diameter equal to about the inner diameter of the delivery lumen for at least a portion of the reinforcing tubular member that extends distal to the proximal guidewire exit port. By extending the reinforcing tubular member distal to the guidewire exit port in this manner, the catheter will have improved columnar strength (i.e. it will resist buckling while being advanced, or pushed, toward the desired treatment site) and pushability. The guidewire receiving lumen and the delivery lumen should be in a parallel relationship. This allows for the reinforcing tubular member to extend distal to the proximal guidewire exit port, while maintaining an outer diameter equal to about the inner diameter of the delivery lumen to provide structural support about the circumference of the lumen distal to the proximal guidewire exit port.

The distal section of the catheter includes at least a guidewire receiving lumen and a delivery lumen. In an aspect of the invention, the guidewire receiving lumen extends from the proximal end of the distal section to the distal end of the distal section. The guidewire receiving lumen may also extend from the proximal end of the distal section to a point proximal of the distal end. The delivery lumen extends from the proximal end of the distal section to the distal end thereof, or to a point proximal of the distal end. The distal section delivery lumen is in fluid communication with the proximal section delivery lumen and the distal section guide wire receiving lumen is in fluid communication with the proximal section guide wire receiving lumen.

DESCRIPTION OF THE DRAWINGS

The operation of the present invention should become apparent from the following description when considered in conjunction with the accompanying drawings, in which:

FIG. 1 is a longitudinal view of a catheter according to the invention.

FIG. 2 is a cross-section of the catheter of FIG. 1, taken along lines 2-2 in FIG. 1.

FIG. 3 is a cross-section of the catheter of FIG. 1, taken along lines 3-3 in FIG. 1.

FIG. 4 is a cross-section of the catheter of FIG. 1, taken along lines 4-4 in FIG. 1.

FIGS. 5 and 5A are longitudinal cross-sections of a portion of a catheter according to the invention.

FIG. 6 is a longitudinal view of a catheter according to the invention.

FIG. 7 is a cross-section of the catheter of FIG. 6, taken along lines 7-7 in FIG. 6.

FIG. 8 is a cross-section of the catheter of FIG. 6, taken along lines 8-8 in FIG. 6.

FIG. 9 is a longitudinal view of a catheter according to the invention.

FIG. 10 is a cross-section of the catheter of FIG. 9, taken along lines 10-10 in FIG. 9.

FIG. 11 is a cross-section of the catheter of FIG. 9, taken along lines 11-11 in FIG. 9.

DETAILED DESCRIPTION OF THE INVENTION

Figure 5A:
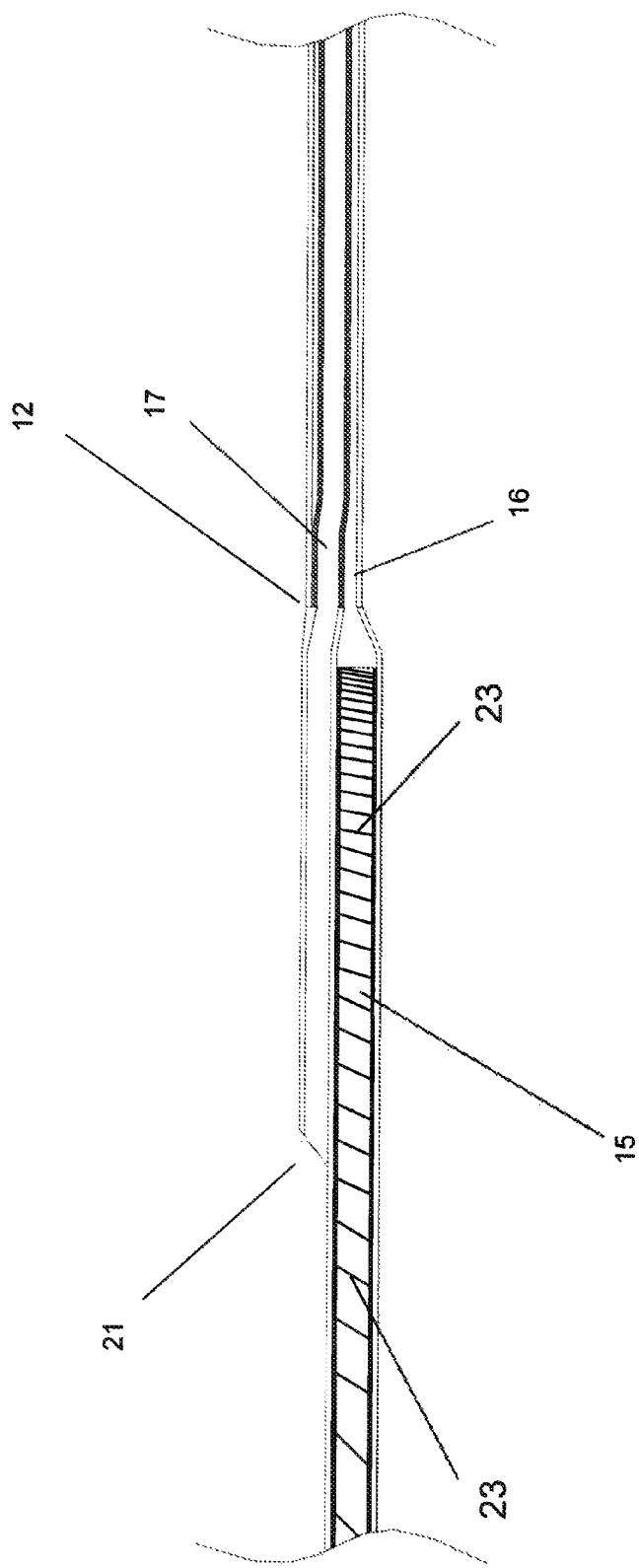

The invention may best be understood with reference to the Figures wherein certain preferred embodiments are set forth in detail.

Turning to FIG. 1 there is shown a rapid-exchange type balloon catheter 10. Typically located on the proximal end of such a catheter is hub assembly 11. As can be seen catheter 10 includes a proximal section and a distal section in this case joined in abutting relationship at joint 12. The proximal section and distal section can be joined in any suitable manner, such as adhesively joined, fused, welded, etc. In an aspect of the invention the proximal and distal sections are butt welded, glued, etc. together so as to form a smooth joint without one section overlapping the other, and without a transition piece, such as a hollow tube, fitted over each piece. As shown in FIG. 2, proximal section includes an outer wall material 14 (such as a plastic material, or other suitable material) and reinforcing tubular member 15 supporting the outer wall 14. The proximal section also includes delivery lumen 16 extending from the proximal end to the distal end of the proximal section.

Close to its distal end, proximal section also includes guidewire receiving lumen 17 in parallel relationship with delivery lumen 16, as shown in FIG. 3. Guidewire receiving lumen 17 extends distally from proximal guidewire exit port 21 to the distal end of the proximal section. Guidewire receiving lumen 17 and delivery lumen 16 remain parallel from proximal guidewire exit port 21 to the distal end of the proximal section. In an aspect of the invention reinforcing tubular member 15 extends from the proximal end, past proximal guidewire exit port 21, to the distal end of the proximal section. Reinforcing tubular member 15 can continuously increase in flexibility from its proximal end to its distal end. Reinforcing tubular member 15 has an outer diameter equal to about the inner diameter of the delivery lumen 16 for at least a portion of the length of the reinforcing tubular member 15 that extends distal to the proximal guidewire exit port 21. In an aspect of the invention reinforcing tubular member 15 has an outer diameter equal to about the inner diameter of the delivery lumen 16 over the entire length of the reinforcing tubular member 15.

As shown in FIG. 4, the distal section includes guidewire receiving lumen 17, defined by tubular member 19, and delivery lumen 16 defined by the annular space between tubular member 18 and tubular member 19. Guidewire receiving lumen 17 extends from the proximal end of the distal section through balloon 13 to the distal end of the distal section, terminating at distal guidewire exit port 20. The delivery lumen 16 extends from the proximal end of the distal section to the proximal end of balloon 13. The delivery lumen 16 is in fluid communication with the interior of balloon 13, so that inflation fluid can be delivered to inflate the balloon 13. Balloon 13 can be sealed or otherwise joined to the distal end of tubular member 18 and to a point near the distal end of tubular member 19 in any suitable manner, as is known to the skilled artisan. Moreover, stent 23 may be provided over balloon 13.

As shown in FIG. 5, in an aspect of the invention guidewire receiving lumen 17 and delivery lumen 16 can be in parallel relationship at the proximal end of the distal section and then transition from being parallel to being coaxial as each lumen extends toward the distal end of the distal section. Moreover, reinforcing tubular member 15 has an outer diameter equal to about the inner diameter of the delivery lumen 16 and extends distally past proximal guidewire exit port 21, contacting the inner wall around the circumference of the delivery lumen 16.

Typically, the catheter shown in FIG. 1 will have an overall length of about 145 to 150 cm (including the hub assembly). The proximal section typically measures about 115 to 125 cm in length. The distal section typically measures about 20 to 30 cm in length. The proximal guidewire exit port is desirably located about 24 to 34 cm from the distal tip of the catheter. Of course, the proximal guidewire port can be located closer to, or further from, the distal tip if desired, including guidewire exit ports less than about 10 cm from the distal tip of the catheter. Unlike prior art rapid-exchange catheters, catheters according to the invention can be produced where there is no significant difference in deliverability based on the location of the proximal guidewire exit port. The performance of the catheter is dominated by the properties of the reinforcing tubular member, and the location of the proximal guidewire exit port does not then cause a defect in the mechanical structure of the device.

Typical lumen dimensions for a coronary application would be 0.018" nominal ID for the guidewire lumen and an 0.023" ID for the delivery lumen, with wall thicknesses of 0.003" minimum. Typical materials would include Nylon or Pebax of various grades or durometers. A reinforcing tubular member of 304 SS could then have an OD of 0.022" and an ID of 0.016", allowing it to fit in the ID of the delivery lumen. The reinforcing tubular member flexibility can be enhanced by the addition of a spiral cut 23 as shown in FIG. 5. FIG. 5A shows how the spiral cut 23 can be graduated by the use of a varying pitch in the cut of about, for example, 10 mm, continuously decreased to a final pitch of about 1 mm, which can then be extended for any desired length; this is particularly useful for devices intended for coronary applications. One knowledgeable in the art will notice that this invention allows for great flexibility in design. A wide range of materials and sizes, including systems for 0.010", 0.014", 0.018", 0.033" or any other guidewire size can be designed utilizing this invention.

Reinforcing tubular member 15 can be any suitable material. In an aspect of the invention the reinforcing tubular member comprises a polymer material. In a further aspect of the invention reinforcing tubular member comprises a metal, such as a hypotube. Reinforcing tubular member 15 is located within the delivery lumen of the proximal section and may extend from a point near the proximal end of the proximal section to a point distal thereto. In an aspect of the invention the reinforcing tubular member extends continuously from the proximal end to the distal end of the proximal section. Moreover, the reinforcing tubular member 15 is configured or constructed or otherwise altered so that the reinforcing tubular member becomes relatively more flexible from a proximal point to a distal point thereon. In an aspect of the invention the reinforcing tubular member 15 transitions from rigid to relatively flexible in a continuous manner. In a further aspect of the invention the reinforcing tubular member 15 transitions continuously from rigid to relatively more flexible from its proximal end to its distal end. Transition from rigid to relatively more flexible can be accomplished in any suitable manner. For example, the distal end of the reinforcing tubular member could have a reduced wall thickness, compared to the proximal end thereof. Moreover, the tubular member could be spirally scored or cut (preferably cut completely through the wall of the tube), with pitch being decreased toward the distal end of the tubular member to result in a tubular member being more flexible at its distal end, as compared to its proximal end. In an aspect of the invention, the tubular member can be cut along only a portion of the tubular member, preferably near the distal end thereof. The tubular member can also be cut along its entire length, with pitch being varied over a part of the tubular member, or along the entire tubular member. The tubular member can be configured so that the portion of the tubular member that extends from a point proximal of the proximal guidewire exit port to a point distal to the proximal guidewire exit port can have the same flexibility or it can increase in flexibility as it extends distal to the guidewire exit port. For coronary applications a 0.022 inch OD×0.016 inch ID 304 stainless steel hypotube can be used. A final pitch of about 1 mm can provide desirable flexibility. A starting pitch of about 10 mm can provide a particularly smooth transition. Furthermore, tube stiffness can be varied by combining two or more materials of varying stiffness and joining them together to form a tubular member of varying stiffness. Of course, any combination of tube wall thickness, spirally scored or cut tubing, pitch variations, and tube materials could be used to obtain a reinforcing tubular member having increased flexibility gradient measured from a proximal point to the distal point thereof. In an aspect of the invention the reinforcing tubular member may be adhered or attached to the inner wall of the delivery lumen at any number of points along the length of the lumen. In an alternative embodiment einforcing tubular member may be adhered or attached to the inner wall of the delivery lumen at only one point (e.g., at the proximal end of the delivery lumen). In a further alternative embodiment, the reinforcing tubular member could be in the form of a wire, tubular braid which transitions from relatively rigid to relatively flexible as it extends from a proximal point to a distal point. The wire, tubular braid could be embedded in the wall material that forms the delivery lumen of the proximal section of the catheter. For example, the wire, tubular braid could be imbedded in a suitable plastic tubular material.

In an alternative embodiment, catheter 10 can be provided with a guidewire receiving lumen that extends for the length (or most of the length) of the proximal section of the catheter. In this embodiment the proximal section still includes delivery lumen 16 in parallel relationship with guidewire receiving lumen 17. However, guidewire receiving lumen 17 can be provided with at least a second proximal guidewire exit port located proximally from the first proximal guidewire exit port 21. In an aspect of this embodiment the at least second proximal guidewire exit port is located at the proximal end of the proximal section, thus resulting in the so-called "convertible catheter" design. In any event, reinforcing tubular member 15 still extends to a point distal to the first proximal guidewire exit port 21. In a further aspect the at least second proximal guidewire exit port is located between the first guidewire exit port 21 and the proximal end of the proximal section of the catheter. In this aspect, the reinforcing tubular member 15 can extend distally past the most proximal guidewire exit port, past the most distal guidewire exit port, or to the distal end of the proximal section of the catheter.

Turning to FIG. 6 there is shown a catheter according to the invention which is of the "convertible" type balloon catheter. The catheter includes proximal section and distal section substantially as set forth in FIGS. 1-4, except that the guidewire receiving lumen 17 of the proximal section extends substantially the length of the proximal section. Moreover, Y connector 30 is provided at the proximal end of the catheter. In addition to first proximal guidewire exit port 21, also provided are second 22 and third (not shown) proximal guidewire exit ports. Second proximal guidewire exit port 22 is located proximally from first proximal guidewire exit port 21 and third proximal guidewire exit port is located at the proximal end of the proximal section. Thus, it can be seen that the catheter of this embodiment can be used in the well known "over-the-wire" mode by threading the guidewire through the distal guidewire exit port 20, past the first and second proximal guidewire exit ports, and exit out the third proximal guidewire exit port. The catheter of this embodiment can also be used in the "rapid-exchange" mode by threading the guidewire through the distal guidewire exit port and through either the first or second proximal guidewire exit port.

Of course, it should be understood that further proximal guidewire exit ports could be provided at any point along the guidewire receiving lumen between the first proximal guidewire exit port 21 and the third proximal guidewire exit port. This would allow the physician to choose between "over-the-wire" mode and "rapid-exchange" mode wherein the "rapid-exchange" feature could comprise many guidewire exit ports which may be utilized depending upon various factors confronting the physician.

Reinforcing tubular member 15 has an outer diameter equal to about the inner diameter of the delivery lumen 16 and extends from near the proximal end of the proximal section to a point distal to the proximal guidewire exit port 21.

A further variation of the "convertible catheter" embodiment is exemplified in FIG. 9. FIG. 9 shows a catheter according to the teaching of commonly owned and copending U.S. patent application Ser. No. 10/402,083, which has been modified according to the present invention. Catheter 30 has proximal and distal sections joined together in abutting relationship at joint 12. Located at the proximal end of the catheter is Y connector 30. As can be seen in FIG. 10, proximal section includes parallel extending guidewire receiving lumen 17 and delivery lumen 16. Guidewire receiving lumen 17 comprises a longitudinally extending channel provided with thin cover material 31, in this case coaxially wrapped about the proximal section of the catheter. Thin cover material 31 can be any suitable material that is capable of being pierced, punctured, etc. to form a guidewire exit port therein. Thus, a proximal guidewire exit port can be made by the physician at virtually any point along the length of the proximal section of the catheter. Preferably the thin cover material 31 is selected from those disclosed in commonly owned and copending U.S. patent application Ser. No. 10/402,083. Delivery lumen 16 has located therein reinforcing tubular member 15 which transitions from relatively rigid at a proximal point to relatively more flexible at a point distal thereto. Reinforcing tubular member 15 extends from near the proximal end of the proximal section to near the distal tip of the proximal section and has an outer diameter equal to about the inner diameter of the delivery lumen 16 over its entire length and, thus, provides structural support to the delivery lumen 16 essentially over the entire length of the proximal section. Distal section includes delivery lumen 16 extending from the proximal end thereof into fluid communication with the interior of balloon 13, which is mounted on the distal end of the catheter. As can be seen in FIG. 11, at least a portion of delivery lumen 16 is defined by the annular space between tubular members 18 and 19. Moreover, distal section also includes guidewire receiving lumen 17 defined by tubular member 19 that extends from the proximal end thereof to the distal end thereof, terminating at distal guidewire exit port 20. Distal section delivery lumen 16, and distal section guidewire receiving lumen 17 can be in parallel relationship at the proximal end of the distal section and transition to a coaxial relationship as the lumens extend toward the distal end of the distal section. Any suitable means may be used to join together the proximal and distal sections, or the catheter assembly may be a single extrusion as discussed above. As seen, the outer diameters of the proximal section and the distal section are joined together in such a manner as to form a smooth outer profile transition from proximal section to distal section.

Although balloon angioplasty catheters have been described in detail, the invention also includes catheters other than balloon angioplasty catheters. For example, the balloon on the distal end of the catheter could be provided with a stent, which can be delivered to a treatment site, as is well known in the art. Further, rather than using a balloon expandable stent, self-expanding stents can be delivered using the catheter of the invention. Such a catheter would include guidewire receiving lumen and delivery lumen, as discussed above. However, rather than terminating at a proximal end of a balloon, the delivery lumen could extend to the distal tip of the catheter. The self-expanding stent could be advanced through the delivery lumen to the treatment site and the catheter withdrawn as the self-expanding stent is held stationary. The stent would then expand against the vessel wall as the catheter is withdrawn. Furthermore, the delivery lumen could be used to deliver any number of devices or treatments to a treatment site. For example, analytical devices and/or other therapeutic devices could be advanced through the delivery lumen to a treatment site. Moreover, ultra sound devices, fiber optics, stent grafts, embolic filters, radiopaque contrast material, medicines, etc. could be delivered via the delivery lumen of the catheter of the invention.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A catheter comprising:
a proximal section having a proximal end and a distal end and at least two parallel, side-by-side extending lumens including a delivery lumen having an inner diameter extending substantially from the proximal end to the distal end and a guidewire receiving lumen, the guidewire receiving lumen having a proximal guidewire exit port at a location distal to the proximal end;
a reinforcing tubular member having a wall and proximal and distal ends, said reinforcing tubular member located in the proximal section delivery lumen extending from substantially the proximal section proximal end to a point distal to the proximal guidewire exit port, wherein the reinforcing tubular member is spirally cut through at least a portion of its wall wherein the spiral cut has a pitch that continuously decreases from the proximal end to the distal end and thereby transitions from relatively rigid to relatively more flexible from a proximal point to a distal point thereon and has an outer diameter equal to about the inner diameter of the delivery lumen for the entire length-of the reinforcing tubular member;
a distal section having a proximal end and a distal end and having at least a distal section guidewire receiving lumen and a distal section delivery lumen, the distal section guidewire receiving lumen and the distal section delivery lumen being coaxial for at least a portion of the distal section, the distal section guidewire receiving lumen being in fluid communication with the distal end of the guidewire receiving lumen of the proximal section and the distal section delivery lumen being in fluid communication with the distal end of the delivery lumen of the proximal section; and
a balloon located at the distal end of the distal section, the balloon having an interior in fluid communication with the delivery lumen.

2. The catheter of claim 1, wherein the proximal guidewire exit port is located less than about 10 cm from the distal end of the distal section of the catheter.

3. The catheter of claim 1, wherein the proximal guidewire exit port is located greater than about 10 cm from the distal end of the distal section of the catheter.

4. The catheter of claim 3, wherein the proximal guidewire exit port is located about 24 cm to about 34 cm from the distal end of the distal section of the catheter.

5. The catheter of claim 1, wherein a stent is mounted on the balloon.

6. The catheter of claim 1, wherein the reinforcing tubular member is comprised of at least two materials of varying stiffness.

7. The catheter of claim 1, wherein the reinforcing tubular member transitions from relatively rigid at a point proximal to the proximal guidewire exit port to relatively more flexible at a point distal to the proximal guidewire exit port.

8. The catheter of claim 1, wherein the reinforcing tubular member maintains the same flexibility from a point proximal to the proximal guidewire exit port to a point distal to the proximal guidewire exit port.

9. A catheter comprising:
a proximal section having a proximal end and a distal end and at least two parallel, side-by-side extending lumens including a delivery lumen having an inner diameter extending substantially from the proximal end to the distal end and a guidewire receiving lumen extending substantially from the proximal end to the distal end, the guidewire receiving lumen having a first proximal guidewire exit port located between the proximal end and the distal end and a second proximal guidewire port located at the proximal end;
a reinforcing tubular member having a wall and proximal and distal ends, said a reinforcing tubular member located in the proximal section delivery lumen, wherein the reinforcing tubular member is spirally cut through at least a portion of its wall wherein the spiral cut has a pitch that continuously decreases from the proximal end to the distal end and thereby transitions from relatively rigid to relatively more flexible from a proximal point to a distal point thereon and having an outer diameter equal to about the inner diameter of the delivery lumen for the entire length of the reinforcing tubular member;
a distal section having a proximal end and a distal end and having at least a distal section guidewire receiving lumen and a distal section delivery lumen, the distal section guidewire receiving lumen and distal section delivery lumen being coaxial for at least a portion of the distal section, the distal section guidewire receiving lumen being in fluid communication with the distal end of the guidewire receiving lumen of the proximal section and the distal section delivery lumen being in fluid communication with the distal end of the delivery lumen of the proximal section; and
a balloon located at the distal end of the distal section, the balloon having an interior in fluid communication with the delivery lumen.

10. The catheter of claim 9, wherein the first proximal guidewire exit port is located less than about 10 cm from the distal end of the distal section of the catheter.

11. The catheter of claim 9, wherein the first proximal guidewire exit port is located greater than about 10 cm from the distal end of the distal section of the catheter.

12. The catheter of claim 11, wherein the first proximal guidewire exit port is located about 24 cm to about 34 cm from the distal end of the distal section of the catheter.

13. The catheter of claim 9, wherein a stent is mounted on the balloon.

14. The catheter of claim 9, wherein the reinforcing tubular member is comprised of at least two materials of varying stiffness.

15. The catheter of claim 9, wherein the reinforcing tubular member transitions from relatively rigid at a point proximal to the proximal guidewire exit port to relatively more flexible at a point distal to the proximal guidewire exit port.

16. A catheter comprising:
- a proximal section having a proximal end and a distal end and at least two parallel, side-by-side extending lumens including a delivery lumen having an inner diameter extending substantially from the proximal end to the distal end and a guidewire receiving lumen, the guidewire receiving lumen being defined by a longitudinally extending channel provided with a thin material capable of being punctured by a physician during use to form a proximal guidewire exit port at any of multiple locations distal to the proximal end;
- a reinforcing tubular member having a wall and proximal and distal ends, said reinforcing tubular member located in the proximal section delivery lumen wherein the reinforcing tubular member is spirally cut through at least a portion of its wall wherein the spiral cut has a pitch that continuously decreases from the proximal end to the distal end and thereby transitions from relatively rigid to relatively more flexible from a proximal point to a distal point thereon and extends from substantially the proximal section proximal end to the proximal section distal end and having an outer diameter equal to about the inner diameter of the proximal section delivery lumen for the entire length of the reinforcing tubular member;
- a distal section having a proximal end and a distal end and having at least a distal section guidewire receiving lumen and a distal section delivery lumen, the distal section guidewire receiving lumen and distal section delivery lumen being coaxial for at least a portion of the distal section, the distal section guidewire receiving lumen being in fluid communication with the distal end of the guidewire receiving lumen of the proximal section and the distal section delivery lumen being in fluid communication with the distal end of the delivery lumen of the proximal section; and
- a balloon located at the distal end of the distal section, the balloon having an interior in fluid communication with the delivery lumen.

\* \* \* \* \*